(12) United States Patent
Takahashi et al.

(10) Patent No.: US 7,000,649 B2
(45) Date of Patent: Feb. 21, 2006

(54) WOVEN TUBING FOR STENT TYPE BLOOD VASCULAR PROSTHESIS AND STENT TYPE BLOOD VASCULAR PROSTHESIS USING THE TUBING

(75) Inventors: Yoshikazu Takahashi, Kanagawa (JP); Teruhisa Yamazaki, Fukui (JP); Sobei Wakabayashi, Fukui (JP)

(73) Assignees: Terumo Kabushiki Kaisha, Tokyo (JP); Seiren Co., Ltd., Fukui (JP)

( * ) Notice: Subject to any disclaimer, the term of this patent is extended or adjusted under 35 U.S.C. 154(b) by 191 days.

(21) Appl. No.: 10/390,033

(22) Filed: Mar. 18, 2003

(65) Prior Publication Data

US 2003/0181971 A1 Sep. 25, 2003

(30) Foreign Application Priority Data

Mar. 20, 2002 (JP) .................... 2002-078627

(51) Int. Cl.
*A61F 2/06* (2006.01)

(52) U.S. Cl. .............. 139/387 R; 139/383 R; 623/1; 623/11; 623/12; 623/1.13; 623/1.1

(58) Field of Classification Search ......... 139/383 R, 139/387 R; 623/1, 11, 12, 1.13, 1.1
See application file for complete search history.

(56) References Cited

U.S. PATENT DOCUMENTS

| 5,383,925 | A | * | 1/1995 | Schmitt ............... 623/1.53 |
| 5,800,514 | A | * | 9/1998 | Nunez et al. ......... 623/1.51 |
| 5,904,714 | A | * | 5/1999 | Nunez et al. ......... 139/383 R |
| 5,976,179 | A |   | 11/1999 | Inoue |
| 6,136,022 | A | * | 10/2000 | Nunez et al. ......... 623/1.1 |
| 6,187,033 | B1 | * | 2/2001 | Schmitt et al. ....... 623/1.35 |
| 6,287,335 | B1 |   | 9/2001 | Drasler et al. |
| 6,478,817 | B1 | * | 11/2002 | Schmitt et al. ....... 623/1.35 |
| 6,540,773 | B1 | * | 4/2003 | Dong ................. 623/1.13 |

FOREIGN PATENT DOCUMENTS

EP     1 086 663 A1     3/2001

\* cited by examiner

*Primary Examiner*—John J. Calvert
*Assistant Examiner*—Robert H. Muromoto Jr.
(74) *Attorney, Agent, or Firm*—Burns, Doane, Swecker & Mathis, L.L.P.

(57) ABSTRACT

A woven tubing for use in a stent type blood vascular prosthesis, using a monofilament having a flattening in the range of 1.2–5.0 and a size in the range of 11–250 dtex in at least part of the warp and a stent type blood vascular prosthesis using the tubing are disclosed. The prosthesis combines a shape retaining property that is capable of maintaining its tubular shape without being crushed by the flow of blood with a high liquid tightness that is capable of reducing the leakage of blood to the exterior and allows prevention of the inflow of blood into the lesion.

12 Claims, 4 Drawing Sheets

WOVEN TUBING FOR STENT TYPE BLOOD VASCULAR PROSTHESIS AND STENT TYPE BLOOD VASCULAR PROSTHESIS USING THE TUBING

BACKGROUND OF THE INVENTION

1. Field of the Invention

This invention relates to a woven tubing for a stent type blood vascular prosthesis and to a stent type blood vascular prosthesis using the woven tubing.

2. Description of Related Art

As a means for the remedy of an aortic aneurysm or an aortic dissection, a method which comprises surgically cutting a lesion in the blood vessel and filling the remaining dent therein with a blood vascular prosthesis has been heretofore regarded as a standard. The surgical operation with ventrotomy or thoracotomy inflicts a large burden of invasion on the patient and entrains danger. In particular on the part of old people who suffer from chronic diseases, the application of this surgical operation has been restricted because of inducing a complication. In recent years, as the cure of aorticaneurysm or aortic dissection with low invasion, an intravascular therapy or surgery has been attracting attention. With the intravascular therapy, it is possible to prevent the inflow of blood to the lesion and protect the lesion against fracture by guiding a blood vascular prosthesis endowed with a stent, namely a stent type blood vascular prosthesis, into the lesion in the blood vessel via a catheter and covering the lesion with the stent blood vascular prosthesis thereby thrombogenesing the lesion.

The stent type blood vascular prosthesis, which is used for this intravascular therapy, is inserted as folded in a small size into the catheter, conveyed to the lesion, and then allowed to unfold and restore the original tubular shape. The term "stent" as used herein refers to a tubular supporting skeleton, which is inserted into an intracorporeal tubular organ such as the blood vessel for supporting the organ. In the blood vascular prosthesis, the stent functions to hold the blood vessel in its tubular shape mechanically and implant the blood vascular prosthesis fast against the wall of the blood vessel. However, the stent type blood vascular prosthesis has limited folding ability and insufficient adaptability to curved blood vessels in human bodies because it is inferior in flexibility to the blood vascular prosthesis that is devoid of stent.

U.S. Pat. No. 5,976,179 discloses an implanting device (equivalent to the "stent type blood vascular prosthesis" designated in the present specification) which has a plurality of intermittently disposed bendable wire rings (equivalent to the "stent" designated in the present specification) concatenated with the tubular surface member (equivalent to the "woven tubing" designated in the present specification). Unlike the conventional stent, which is provided with supporting skeletons concatenated continuously in the direction of length, in the stent disclosed in the publication individual wire rings for constructing such a stent are not concatenated. This stent relies on this construction to attain an implanting device which prevents degradation of flexibility and excels in folding ability and adaptability to curved blood vessels in human bodies. Further, by using a monofilament having a shape retaining property as warps and a dense multifilament as wefts in the surface member, the surface member is aimed at attaining such a shape retaining property as avoids being crushed by the flow of blood and such a liquid tightness (low water permeability) as avoids leakage of blood to the exterior in the implanting devices even when the wire rings are not concatenated.

SUMMARY OF THE INVENTION

The implanting device mentioned above is characterized by the combination of the wire rings and the surface member. That is to say, the wire rings themselves have no ability whatever to resist the crush exerted in the direction of the length of the device. When the wire rings are combined with the conventional surface member which pays no consideration to the crush, therefore, this combination could possibly constitute a fatal defect because the flow of blood crushes the implanting device and the blood flows through the gap in the terminal part into the lesion.

The use of a monofilament for warps, however, has given rise to another problem that the interlacing parts of warps and wefts are liable to form gaps. Generally, when a multifilament is used for both warps and wefts, the interlacing parts do not easily form gaps because the cross sections of such a multifilament in the interlacing parts are deformed into elliptical shapes or depressed shapes and consequently enabled to induce mutual adhesion of the relevant warps and wefts. In contrast, when a monofilament is used for either or both of warps and wefts, the formation of gaps is apt to occur because the cross sections of such a monofilament are not deformed even in the interlacing parts and the warps and the wefts cannot be brought into mutual adhesion. The gaps between the warps and the wefts may cause a marked decline in the liquid tightness. The surface member which uses the monofilament for the warps thereof has no sufficient liquid tightness even when it uses a dense multifilament for the wefts thereof, and does not prevent the inflow of blood into the site of a lesion due to leakage of blood. Thus, it has obstructed the cure of an aortic aneurysm or an aortic dissection.

This invention has been produced in view of such true state of prior art.

An object of this invention is to provide a woven tubing for a stent type blood vascular prosthesis (It may be referred to simply as "WTVP".), which combines a shape retaining property that is able to retain the tubular shape thereof without being crushed by the flow of blood with a high liquid tightness enough to reduce the leakage of blood to the exterior when it is implanted at the site of a lesion as a stent type blood vascular prosthesis (It may be simply referred to as "SBVP".) and allows prevention of the inflow of blood into the lesion.

Another object of this invention is to provide a SBVP that uses the WTVP mentioned above.

We have frequently pursued a diligent study with a view to solving the problems mentioned above. Consequently, we have found that it is highly effective in accomplishing the objects mentioned above to use a monofilament that satisfies specific flattening and size for the warps in the WTVP. The present invention has been achieved as a result. This invention is constructed as follows.

A WTVP is characterized by using a monofilament having a flattening in the range of 1.2–5.0 and a size in the range of 11–250 dtex in at least part of the warps.

A SBVP is characterized by comprising a tubing set forth in the above and a stent.

The WTVP of this invention, owing to the use of a monofilament satisfying specific flattening and size for the warps of the WTVP, accomplishes a shape retaining property that is able to retain the tubular shape thereof without being crushed by the flow of blood and a high liquid tightness enough to reduce the leakage of blood to the exterior when it is implanted at the site of a lesion as a SBVP. As a result, it is possible to prevent the inflow of blood into the site of a lesion.

The WTVP of this invention can be favorably applied even to such a stent as produces by itself no durability to withstand the crush in the direction of length to give rise to a SBVP excelling in flexibility and conformability. It is, therefore, highly useful for the intravascular therapy.

The above and other objects, features and advantages of the present invention will become clear from the following description of the preferred embodiments.

BRIEF DESCRIPTION OF DRAWINGS

The accompanying drawing incorporated in and forming a part of the specification, illustrates several aspects of the present invention, and together with the description serve to explain the principles of the invention. In the drawings:

FIG. 2 is a cross section explaining the state of contact between warps and wefts; 2A depicting the product of this invention and 2B the conventional product;

DETAILED DESCRIPTION OF THE PREFERRED EMBODIMENTS

Now, this invention will be described below with reference to embodiments. The term "woven tubing" refers to a tube obtained by joining the opposite edges of a flat woven fabric by sewing or fusion, or a tube formed from the stage of weaving by the technique of hollow weave, namely by having a weft woven spirally in the circumferential direction between warps disposed along the direction of length.

The WTVP of this invention is characterized by using in at least part of the warps a monofilament that satisfies a flattening in the range of 1.2–5.0 and a size in the range of 11–250 dtex. The WTVP is enabled, by the stiffness of the monofilament, to acquire a shape retaining property that defies the crush by the flow of blood and, by the sectional shapes of the monofilament, to acquire a high liquid tightness enough to reduce the leakage of blood to the exterior.

Figure 1:
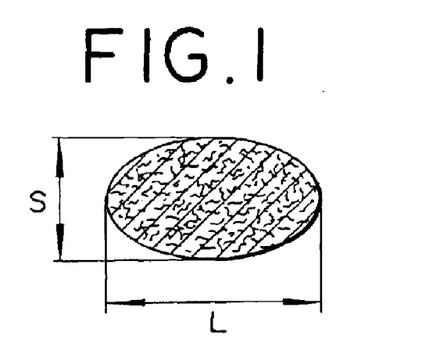
FIG. 1 is a cross section illustrating the section of a thread to explain the flattening of a thread.
Figure 2A:
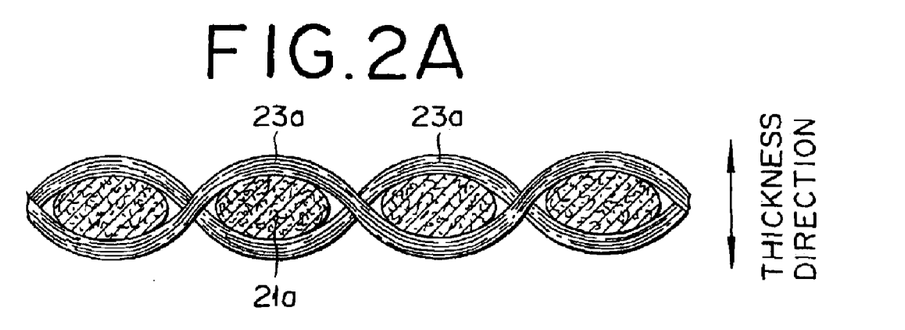
Figure 3:
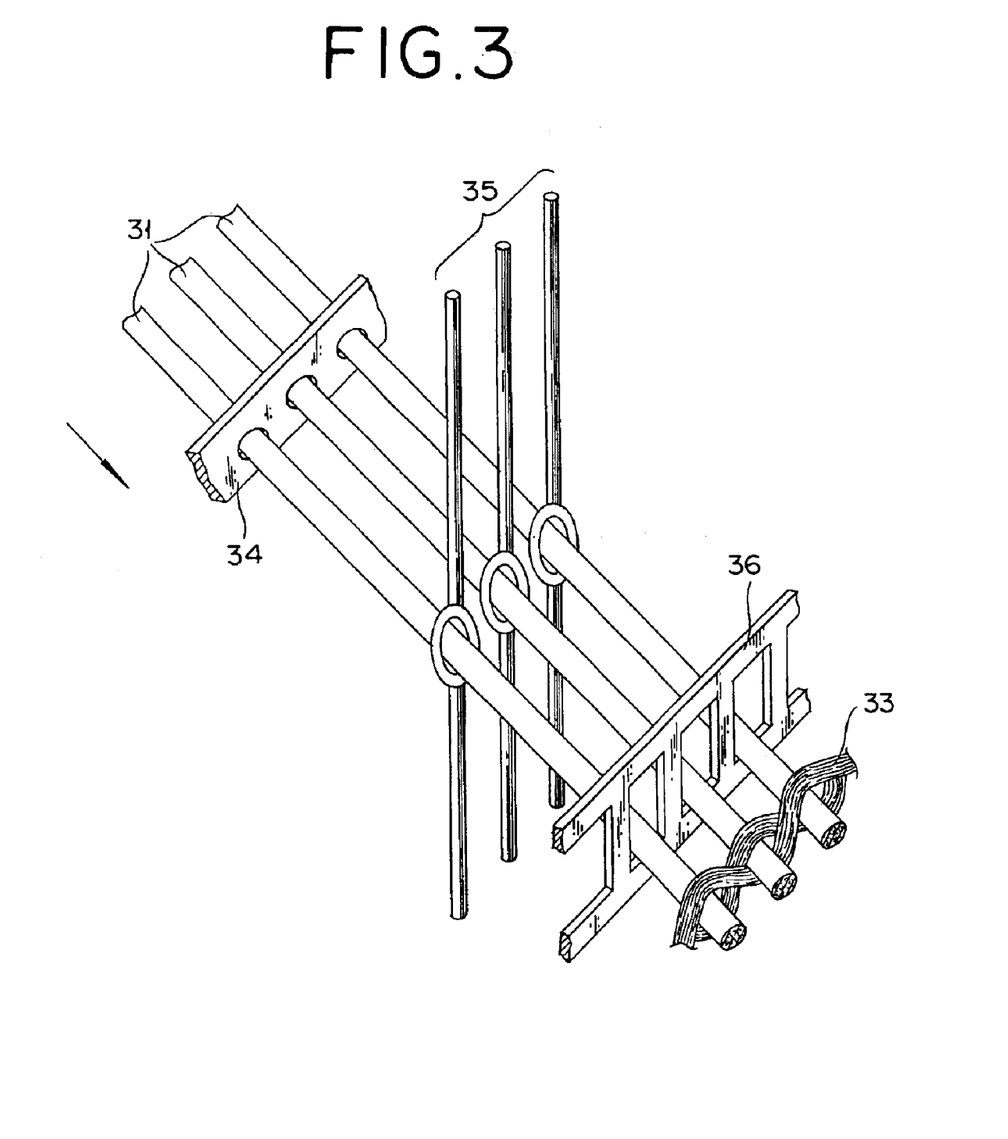
FIG. 3 is a diagram explaining the method for arraying warps in such a state that the short sides of warps lie along the direction of thickness of a woven fabric.
Figure 4A:
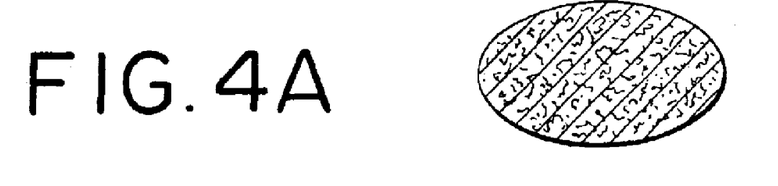
FIG. 4 is a diagram illustrating the sectional shapes of threads.
Figure 4B:
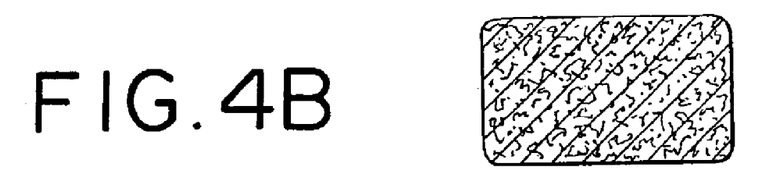
Figure 4C:
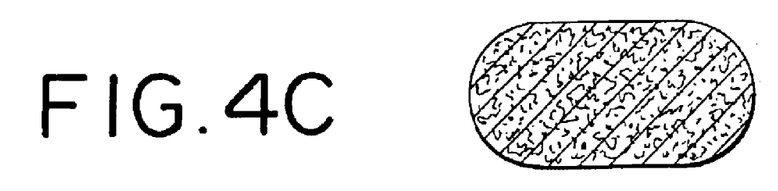
Figure 4D:
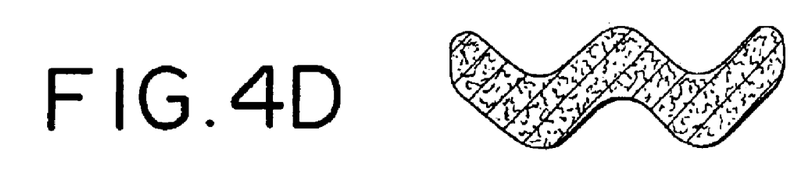
Figure 4E:
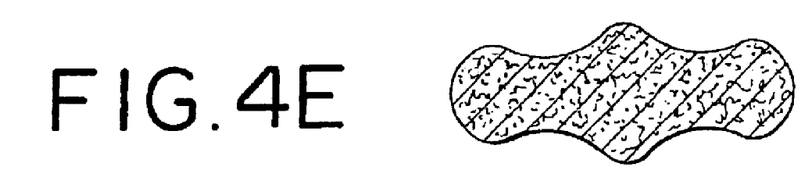

The monofilament to be used in the warps has a flattening in the range of 1.2–5.0, preferably 1.5–3.0. FIG. 1 is a cross section illustrating the section of a thread. In FIG. 1, the term "flattening" refers to the quotient of the long side L divided by the short side S in a rectangle when circumscribed the section of a thread. The flattening is such that the section of the thread is more elongated or flattened in proportion as the numerical value thereof increases. FIG. 2A is a diagram depicting the relation between the sections of warps and the wefts in the woven fabric of the WTVP. In FIG. 2A, monofilaments 21a, which are warps, are disposed in such a state that the short sides of warps 21a lie along the direction of thickness of the woven fabric by means of wefts 23a. FIG. 3 is a diagram explaining a method for arraying the short sides of the warps along the direction of thickness of the woven fabric. In FIG. 3, warps 31 are passed through a separator 34 before they are supplied to the weaving part at which they are interlaced with wefts 33. Specifically, for the purpose of so disposing the warps 31 as to make the short sides thereof lie along the thickness of the woven fabric, the warps 31 may be passed through holes such as a separator 34, a heald 35, and a reed 36 before they are supplied to the weaving part. In FIG. 3, the warps and the wefts are magnified rather than the others for readily looking. If the flattening is smaller than 1.2, the WTVP using the monofilament in at least part of the warps, will form gaps between warps and wefts, betray deficiency in liquid tightness, and fail to prevent the leakage of blood. Further, the wall thickness of the WTVP increases in proportion as the magnitude of the flattening approaches 1. If the flattening is larger than 5.0, the excess will result in impairing the thread forming property and the weave forming property and degrading the stability of the commercial aspect of the operation. So long as the relation of the specific flattening is satisfied, the sectional shape of the thread is not particularly restricted but may be selected from the group consisting of elliptic, rectangle, flat plate, W-shaped plate, and corrugated plate. FIG. 4 is a cross section illustrating various sectional shapes of threads; 4A depicting an elliptic shape, 4B a rectangular shape, 4C a flattened shape, 4D a W-letter shape, and 4E a corrugated shape.

The monofilament has a size in the range of 11–250 dtex, preferably 30–80 dtex. If the size is smaller than 11 dtex, the shortage will result in impairing the weaving property, degrading the stability of the commercial aspect of the operation, and decreasing the stiffness. The WTVP using the monofilament in at least part of the warps and the SBVP using the WTVP fail to acquire a sufficient shape retaining property and fail to manifest durability enough to withstand the crush in the direction of length. If the size exceeds 250 dtex, the excess will result in increasing the wall thickness of the WTVP and unduly enlarging the stiffness and consequently rendering the WTVP and a SBVP using the WTVP difficult to fold them in a small size. As a result, the catheter to be used for the intravascular therapy will be required to have a large diameter such that it may not be easily inserted into the blood vessel or moved therein and worse still may possibly inflict an injury to the site of a lesion.

By using the monofilament having the flattening and the size fall within the respectively specific ranges (may be referred to as "the present monofilament" hereinafter) in at least part of the warps, it is possible to obtain a WTVP which combines a shape retaining property that is able to retain the tubular shape thereof without being crushed by the flow of blood with a high liquid tightness enough to reduce the leakage of blood to the exterior when it is implanted at the site of a lesion as a SBVP and allows prevention of the inflow of blood into the lesion. For the purpose of producing the monofilament of this description, any of the spinning methods heretofore known to the art may be adopted and a spinning nozzle conforming in shape and diameter of orifice, for example, to the sectional shape and the size of the monofilament aimed at may be selected.

The strands or threads other than the monofilament that is used in the warps (which may be occasionally referred to as "other threads") are not particularly restricted. For example, the multifilament heretofore used as the raw material for the blood vascular prosthesis, namely formed of 10–1000 single filaments having a single filament size in the range of 0.1–3.5 dtex, may be used as "other threads."

If the size of the single filament is smaller than 0.1 dtex, the WTVP will be deficient in strengths such as tensile strength and bursting strength. If the size of the single filament exceeds 3.5 dtex, the single filament, when used in combination with the present monofilament, will render the WTVP and a SBVP using the WTVP difficult to be folded in a small size because of an increased wall thickness and an increased stiffness.

The shape of section of the single filament is not particularly restricted. The section may be in a circular or irregular shape.

If the number of the single filament is smaller than 10, the WTVP will betray deficiency in liquid tightness and fail to prevent the leakage of blood. If the number exceeds 1000, the filament will tend to incur troubles such as warp breakage and fluff during the course of weaving and impair the operational stability.

The multifilament constructed as described above are preferred to have a total size in the range of 33–110 dtex. If the total size is smaller than 33 dtex, the WTVP, combined with the present monofilament, will betray deficiency in strengths such as tensile strength and bursting strength. If the total size is larger than 110 dtex, the WTVP and a SBVP using the WTVP will not be easily folded in a small size because of an increased wall thickness and an undue addition to stiffness.

The other threads to be used in the warps may be properly selected from the multifilament mentioned above, preferably a multifilament which has a similar total size to the present monofilament to be combined. If the monofilament to be used in the warps is notably different in a size from the other threads to be used in the warps, the WTVP will form a nonuniform surface and possibly betray deficiency in liquid tightness. It will further entail wide dispersion of strengths such as tensile strength and bursting strength and of wall thickness as well.

Twist multiplier of the multifilament is preferred to be in the range of 0–1000 times/meter. The smaller the twist multiplier, the less the mutual entangling and the overlapping of the single filaments occur. Thus, the liquid tightness is enhanced. The twist multiplier of not more than 1000 times/meter is allowable from the viewpoint of the stability of weaving. If the twist multiplier exceeds 1000 times/meter, the mutual entangling and the overlapping thereof will have adverse influences and then the WTVP will have insufficient liquid tightness. The twist multiplier of the multifilament is preferred to be in the range of 200–500 times/meter for the sake of the balance between the stability of weaving and the liquid tightness.

The ratio of the present monofilament to the other threads in the warps is preferred to be in the range of 25:75–100:0 on the assumption that the total number of warps forming the WTVP is 100. The other threads and the monofilament are preferred to be disposed uniformly. If the ratio is smaller than 25:75, the WTVP and a SBVP using the WTVP will not acquire a sufficient shape retaining property and will offer no sufficient durability to withstand the crush in the direction of length. By adjusting the ratio in the range of 25:75–100:0, it is possible to adjust such a durability. That is to say, the durability of the WTVP and a SBVP using the WTVP increases in accordance as the ratio the monofilament is increased.

The wefts for forming the WTVP are not particularly restricted. Similarly to the other threads to be used in the warps, the following multifilament may be used as the wefts: a multifilament which has been heretofore used as the raw material for the blood vascular prosthesis, i.e. a multifilament having a single filament size in the range of 0.1–3.5 dtex, preferably 0.1–1.0 dtex, and formed of 10–1000 single filaments. If the size of the single filament is in the range of 0.1–1.0 dtex, the WTVP will gain further in denseness and enjoy enhanced liquid tightness. The multifilament having a total size in the range of 33–110 dtex and a twist multiplier in the range of 0–1000 times/meter, preferably 200–500 times/meter prove particularly advantageous.

The sectional shape of the single filament is not particularly restricted. The section may be in a circular or irregular shape.

By using the multifilament satisfying the conditions mentioned above in the wefts of the WTVP, it is possible to make the most of the liquid tightness, which is one of the merits of this invention, without impairing strengths such as tensile strength and bursting strength and folding ability.

Though the raw material for the present monofilament to be used in warps, other threads to be used in warps, and threads to be used in wefts of the WTVP of this invention is not particularly restricted, it is preferred to be polyester type fibers from the actual results of use as the material for a blood vascular prosthesis. The polyester type fibers have been widely used as the raw material for blood vascular prosthesis because they have chemical stability, great durability, and high mechanical strength and avoid exhibiting toxicity or producing any foreign body reaction. As examples of polyester type fibers, polyethylene terephthalate, polybutylene terephthalate, polyester-polyether block copolymers, and composite fibers thereof may be cited.

The textile design of the WTVP is not particularly restricted but includes, for example, plain weave, twill weave, satin weave, or crepe weave. Among other weaves, the plain weave proves particularly favorable because it permits easy formation of a tubular article having a small wall thickness and excelling in strengths such as tensile strength and bursting strength and in liquid tightness.

The WTVP of this invention, which is obtained as described above, combines a shape retaining property that is able to retain the tubular shape thereof without being crushed by the flow of blood with a high liquid tightness enough to reduce the leakage of blood to the exterior when it is implanted at the site of a lesion as a SBVP. In particular, the WTVP which has the magnitudes of column strength, radius of kink, coefficient of water permeability, and wall thickness within respectively specified ranges, excels not only in the shape retaining property and the liquid tightness which are the salient merits of this invention but also in the kink resistance and the folding ability which ought to be naturally endowed for the SBVP. Thus, it is quite useful for the intravascular therapy.

The column strength of the WTVP is preferred to be in the range of 0.020–0.130 N/mm of diameter. The term "column strength" as used herein represents the strength or durability to withstand the crush in the direction of length. The larger the value of the column strength is, the higher the durability to withstand the crush in the direction of length is. If the column strength is smaller than 0.020 N/mm of diameter, the WTVP, when implanted at the site of a lesion as a SBVP, will be crushed by the flow of blood and compelled to yield to the inflow of blood into the site of the lesion. If the column strength exceeds 0.130 N/mm of a diameter, folding the WTVP and a SBVP using the WTVP into a small size will become difficult because of an increased stiffness. The WTVP or SBVP further will not easily follow the blood vessel after the WTVP or SBVP has been implanted therein.

The radius of a kink in the WTVP varies with the inside diameter thereof and tends to increase in proportion to the size of inside diameters. Though the radius of a kink, therefore, cannot be uniquely defined, it is preferred to be not more than 5.5 mm when the WTVP has an inside diameter of 24 mm, for example. The term "kink" as used herein refers to the phenomenon in which the blood vascular prosthesis is folded under the inner flexure of a body or the external pressure. The kink resistance is expressed by the radius of a kink, namely such a radius of the loop formed in a given blood vascular prosthesis as forms a clearly discernible bend therein. The smaller the value of the radius of a kink is, the larger the durability to withstand the bend is. The radius of a kink is preferred to be as near to 0 mm as possible for the sake of facilitating the insertion and implant of a SBVP using the WTVP even to a complicated bent portion in the blood vessel. The radius of a kink in the WTVP of this invention is preferred to be not more than 5.5 mm when the inside diameter of the WTVP is assumed to be 24 mm. If the radius is larger than 5.5 mm, the SBVP will fail to conform to a curved human blood vessel when the WTVP is implanted at the site of a lesion as a SBVP.

The WTVP of this invention is primarily supposed to be applied to the therapy of an aortic aneurysm or an aortic dissection in combination with a stent. The inside diameter of this WTVP may be in the range of 7–54 mm. On account of the possibility of personal equation, however, it is not limited to this range.

The WTVP is preferred to have undergone a crimp treatment. The application of this crimp treatment improves the WTVP and the SBVP of this invention in the ability of flexion to the extent of enabling them to conform naturally to the shape of a human blood vessel. In other words, the radius of a kink is decreased and the kink resistance is enhanced. Further, the crimps consequently imparted to the WTVP produce an effective action in the restoration of the SBVP using the WTVP from the folded state to the original shape. The method for imparting such crimps to the WTVP may be selected from among the known methods such as those described in U.S. Pat. No. 3,337,673 and JP-A-1-155860.

The coefficient of water permeability of the WTVP is preferred to be not more than 500 mL/min/cm$^2$. The coefficient of water permeability is closely related to the liquid tightness. More preferably, this magnitude is 0 mL/min/cm$^2$ or approximates closely to 0 mL/min/cm$^2$ for the sake of exalting the degree with which the leakage of blood from the WTVP can be prevented and thrombogenesis can be promoted. The upper limit of the preferred coefficient of water permeability is 500 mL/min/cm$^2$. If the coefficient is larger than this upper limit, the WTVP, when implanted in the site of a lesion as a SBVP, will suffer blood to leak therefrom and fail to prevent the inflow of blood into the site of the lesion.

The wall thickness of the WTVP is preferred to be not more than 150 $\mu$m. If the wall thickness is larger than 150 $\mu$m, the WTVP and a SBVP using the WTVP will not be easily folded into a small size. The folding ability, as previously mentioned, is an important parameter in the construction of the SBVP. If the SBVP is deficient in folding ability, it will require the catheter used in the intravascular therapy to have a large diameter and will lower operational efficiency.

The WTVP may be furnished with a branching part. When an aneurysm is formed in a branching part of a vital blood vessel, e.g., from the abdominal aorta to the common iliac artery, it is conceivable to perform the therapy by using a plurality of straight SBVPs, though the relevant surgical operation is complicated and consumes an unduly long time. In this case, the use of a SBVP furnished with a branching part is advantageous and rational from the viewpoint of lightening the burden on the patient and ensuring the safety of the operation.

The WTVP of this invention is preferred to be applied to the stent disclosed in U.S. Pat. No. 5,976,179, namely the stent which, as represented by a stent having wire rings disposed intermittently and made of titanium-nickel alloy et al, is not possessed in itself of the durability to withstand the crush in the direction of length. Further, the WTVP of this invention can manifest more effectively the merit of this invention which resides in excelling in the shape retaining property, though it is not restricted by this manifestation.

Further, owing to the merit of excelling in the shape retaining property and the liquid tightness, the WTVP can be effectively used as a blood vascular prosthesis that is devoid of a stent.

Figure 5:
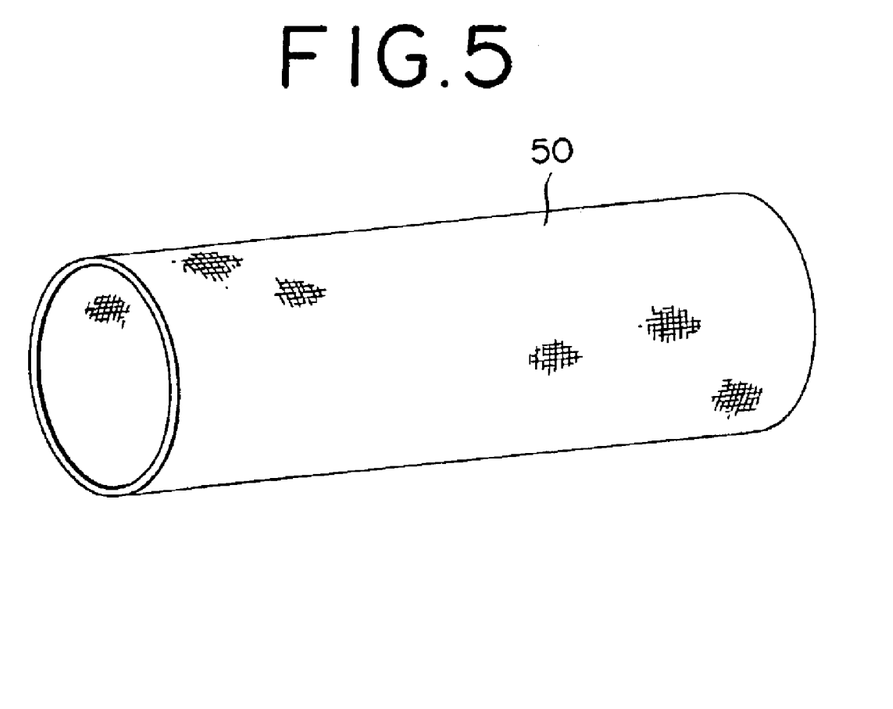
FIG. 5 is a schematic diagram showing a WTVP.

FIG. 5 is a schematic diagram showing a WTVP. In FIG. 5, 50 is a WTVP.

Figure 6:
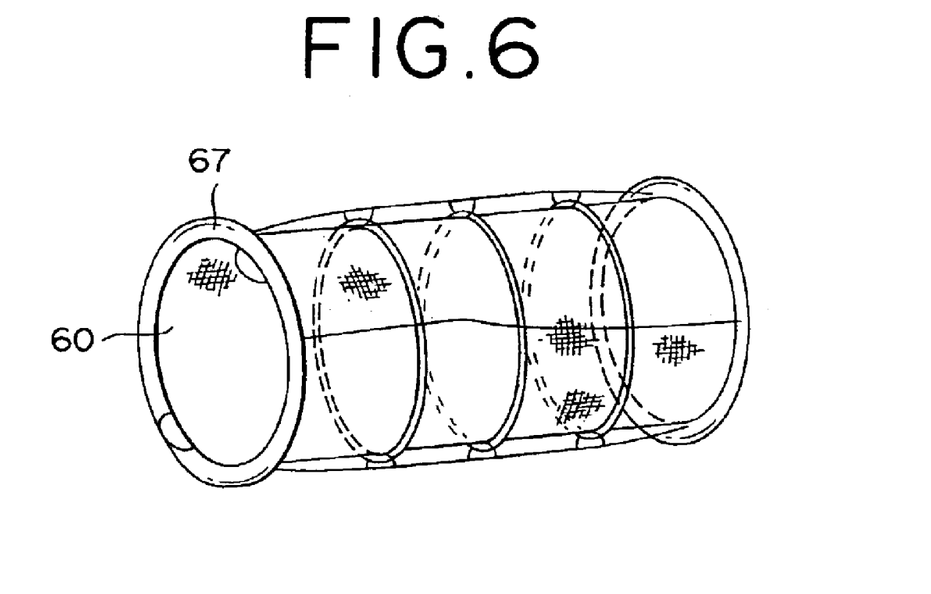
FIG. 6 is a schematic diagram showing a SBVP.

FIG. 6 is a schematic diagram showing a SBVP. In FIG. 6, a WTVP 60 is innerly attached to a stent 67.

EXAMPLE

Now, this invention will be described more specifically below with reference to examples. It should be noted, however, that this invention is not limited to the examples.

Methods of Determination

Column Strength (N/mm in Diameter)

The force required for crushing a sample of woven tubing 50 mm in length to a length of 30 mm is measured with a tensile or compression test machine. The denomination "mm in diameter" denotes the magnitude of the inside diameter of a given WTVP.

Radius of a Kink (mm)

The measurement of this magnitude is performed by consulting ISO7198 Cardiovascular implants-Tubular vascular prostheses. Such a radius of the loop formed in a given woven tubing as formed a clearly discernible fold is measured with a cylindrical jig of a known radius. The retention of the inner pressure of the sample tubing is omitted for rating the characteristics of the woven tubing itself.

Coefficient of Water Permeability (mL/min/cm$^2$)

The measurement of this magnitude is performed by consulting ISO7198 Cardiovascular implants-Tubular vascular prostheses. This magnitude is measured by supplying water under 120 mmHg (16.0 kPa) to the surface of a sample 0.5–1.0 cm$^2$ in area and measuring the quantity of the water which had permeated the sample in one minute. The quantity of permeating water consequently found is reduced to the rate per 1.0 cm$^2$ and reported as the coefficient of water permeation. The determination of the coefficient of water absorption is performed on a sample of woven tubing which has not yet undergone the crimp treatment.

Wall Thickness ($\mu$m)

The measurement of this magnitude is performed with a constant pressure thickness meter by consulting ISO7198 Cardiovascular implants-Tubular vascular prostheses. This measurement is performed on a sample of woven tubing that has not yet undergone the crimp treatment.

Example 1

A tubing measuring 24 mm in inside diameter and having a plain weave design was formed by hollow weave using a monofilament of polyethylene terephthalate having an elliptic cross section, a flattening of 1.2 and a size of 33 dtex (the present monofilament) for warps and a multifilament of polyethylene terephthalate having a circular sectional shape of single filament, a flattening of single filament of 1.0, and a single filament size of 0.55 dtex, formed of 170 single filaments to a total size of 94 dtex, and endowed with a twist multiplier of 200 times/meter for wefts. The tubing was subjected to a crimping treatment to obtain a target WTVP.

Example 2

A target WTVP was obtained by repeating the procedure of Example 1, except that a monofilament of polyethylene terephthalate having an elliptic sectional shape and a flattening of 2.0 and a size of 33 dtex (the present monofilament) was used for warps.

Example 3

A target WTVP was obtained by repeating the procedure of Example 1, except that a monofilament of polyethylene terephthalate having an elliptic sectional shape and a flattening of 5.0 and a size of 33 dtex (the present monofilament) was used for warps.

Example 4

A target WTVP was obtained by repeating the procedure of Example 1, except that a monofilament of polyethylene terephthalate having a depressed sectional shape and a flattening of 5.0 and a size of 250 dtex (the present monofilament) was used for warps.

Example 5

A target WTVP was obtained by repeating the procedure of Example 1, except that a monofilament of polyethylene terephthalate having an elliptic sectional shape and a flattening of 2.0 and a size of 33 dtex (the present monofilament) and a multifilament of polyethylene terephthalate having a circular sectional shape of single filament, a flattening of single filament of 1.0, and a single filament size of 2.8 dtex, formed of 12 single filaments to a total size of 33 dtex, and endowed with a twist multiplier of 300 twists/meter at a ratio of 50:50 were used for warps. In the interlacing parts of warps and wefts, the cross sections of the multifilament (used as part of the warps, and the wefts) were individually deformed into an elliptic shape and the flattening was 2.0 in the warps.

Comparative Example 1

A WTVP was obtained by repeating the procedure of Example 1, except that a monofilament of polyethylene terephthalate having a circular sectional shape and a flattening of 1.0 and a size of 33 dtex was used for warps.

Figure 2B:
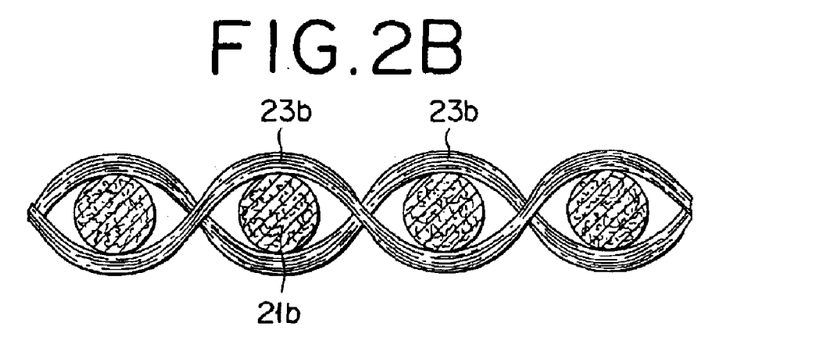

FIG. 2B is a diagram depicting the gaps between warps and wefts in the WTVP obtained in Comparative Example 1. In FIG. 2B, the circular sections of monofilaments, which were warps 21b, were disposed between two multifilaments, which were wefts 23b.

Comparative Example 2

A WTVP was obtained by repeating the procedure of Example 1, except that a monofilament of polyethylene terephthalate having a circular sectional shape and a flattening of 1.0 and a size of 250 dtex was used for warps.

Comparative Example 3

A commercially available blood vascular prosthesis (made of polyethylene terephthalate, measuring 24 mm in inside diameter, formed by hollow weave in plain weave design, and undergone a crimping treatment) was evaluated with respect to performance.

The size and the number of the single filament used in the prosthesis were found as follows. Cross sections of the filament were observed under an electron microscope to find the number and the diameters of the single filament. Then, the size of the single filament was calculated from the diameters of the single filament and the total size was calculated from the size and the number of the single filament. As a result, the warp was found to be multifilaments having a circular sectional shape of single filament, a flattening of the single filament of 1.0, a single filament size of 0.58 dtex and formed of 216 single filaments to a total size of 125 dtex and the weft was found to be multifilaments having a circular sectional shape of single filament, a flattening of the single filament of 1.0, a single filament size of 0.58 dtex, and formed of 144 single filaments to a total size of 84 dtex. In the interlacing parts of warps and wefts, the sections of the threads were individually deformed into an elliptic shape and the flattening was 2.5 in the warps. Incidentally, the coefficient of water permeability and the wall thickness were measured of a blood vascular prosthesis that had been deprived of crimps by a heat treatment.

The results of evaluation performed on WTVPs which were produced in Examples 1–5 and Comparative Examples 1–3 are shown in Table 1.

TABLE 1

| | Construction | | | | | | | | Items of evaluation | | | |
| | Warps | | | | | Wefts | | | | | | |
| | 1a | 1b | 1c | (2) | (3) | 4a | 4b | 4c | (5) | (6) | (7) | (8) |
| Example 1 | 33 | — | — | Ellipse | 1.2 | 94 | 170 | 0.55 | 0.064 | 4 | 400 | 130 |
| Example 2 | 33 | — | — | Ellipse | 2.0 | 94 | 170 | 0.55 | 0.060 | 4 | 150 | 120 |
| Example 3 | 33 | — | — | Ellipse | 5.0 | 94 | 170 | 0.55 | 0.045 | 5.5 | 150 | 100 |
| Example 4 | 250 | — | — | Flat | 5.0 | 94 | 170 | 0.55 | 0.130 | 5.5 | 150 | 150 |
| Example 5 | 33 | — | — | Ellipse | 2.0 | 94 | 170 | 0.55 | 0.029 | 4 | 70 | 120 |
| | 33 50:50 | 12 | 2.8 | Ellipse | 2.0 | | | | | | | |
| Com. Ex. 1 | 33 | — | — | Circle | 1.0 | 94 | 170 | 0.55 | 0.064 | 4 | 800 | 140 |

TABLE 1-continued

|  | Construction | | | | | | | | Items of evaluation | | | |
|---|---|---|---|---|---|---|---|---|---|---|---|---|
|  | Warps | | | | | Wefts | | | | | | |
|  | 1a | 1b | 1c | (2) | (3) | 4a | 4b | 4c | (5) | (6) | (7) | (8) |
| Com. Ex. 2 | 250 | — | — | Circle | 1.0 | 94 | 170 | 0.55 | 0.130 | 4 | 700 | 320 |
| Com. Ex. 3 | 125 | 216 | 0.58 | Ellipse | 2.5 | 84 | 144 | 0.58 | 0.010 | 40 | 50 | 120 |

In Table 1:
(1a): Size (It means total size when it is a multifilament.)
(1b): The number of the single filament (in the case of the multifilament)
(1c): Single filament size (in the case of the multifilament)
(2): Sectional shape
(3): Flattening
(4a): Size (It means total size when it is a multifilament.)
(4b): The number of the single filament (in the case of the multifilament)
(4c): Single filament size (in the case of the multifilament)
(5): Column strength (N/mm in diameter)
(6): Radius of kink (mm)
(7): Coefficient of water permeability (mL/min/cm$^2$)
(8): Wall thickness ($\mu$m)

Example 6

SBVPs were formed by causing wire rings disclosed in U.S. Pat. No. 5,976,179 to be sewn with intervals of 15 mm to WTVPs formed in a total length of 60 mm in Examples 1–5. These SBVPs were each implanted via a catheter into a resinous tube simulating a blood vessel and measuring 24 mm in inside diameter and 28 mm in outside diameter. The position for implanting the SBVP on the inside surface of the resinous tube for implanting the SBVP was curved along the outer periphery of a cylinder 50 mm in radius and a branch was formed on the major curvature side of the position for implanting the SBVP with a tube 10 mm in inside diameter. When the water assumed to be blood was made to flow into the resinous tube, the tube held the inner cavity thereof intact without suffering the shape thereof crushed by the flow of water and leaked no water through the branch. Thus, it could acquire a satisfactory result of implant.

Comparative Example 4

SBVPs were formed by repeating the procedure of Example 6, except that the WTVPs in Comparative Examples 1–3 were used. These SBVPs were each implanted in the same resinous tube as used in Example 6 and the water assumed to be blood was made to flow into the resinous tube.

As a result, the SBVP of Comparative Example 1 induced conspicuous leak of water through the branch because of large coefficient of water permeability, though it did not suffer the shapes to be crushed by the flow of water. Thus, it was suspected to be incapable of satisfactorily blocking the flow of blood into an aneurysm in the case of clinical use.

In Comparative Example 2, the SBVP, owing to a large wall thickness, offered an increased sliding resistance inside a catheter while it was being passed therethrough and rendered the operation of implant difficult. Though this SBVP, similarly to the SBVP of Comparative Example 1, showed no discernible sign of a crush of the shape by the flow of water, it induces a conspicuous leakage of water through the branch owing to a large coefficient of water permeability. Thus, it was suspected to be incapable of satisfactorily blocking the flow of blood into the aneurysm in actual clinical use.

In the SBVP of Comparative Example 3, because of small magnitudes of column strength, the ring at the most proximal portion could not be easily disposed in a stable manner perpendicularly to the tube during the course of implant of the prosthesis in the tube. The SBVP also showed a sign of partial decrease of the cross section of the inner cavity due to the occurrence of a kink. Further, the ring at the most proximal portion showed an inclination of being moved slightly toward the peripheral side by the flow of water. Thus, the SBVP was suspected to have the possibility of starting from the position of implant or inducing blockage of the inner cavity after a protracted implant.

The entire disclosure of Japanese Patent Application No. 2002-078627 filed on Mar. 20, 2002 including specification, claims, drawings, and summary are incorporated herein by reference in its entirety.

What is claimed is:

1. A woven tubing for use in a stent blood vascular prosthesis comprising:

a monofilament having a cross-sectional shape selected from a group consisting of elliptic, rectangle, flat and W-shaped shapes and a size in the range of 11–250 dtex for at least part of warp;

a weft;

wherein the warp and weft are woven; and the cross-sectional shape of the monofilament when woven with the weft reduces leakage of blood to outside the woven tubing by reducing gaps between the warp and the weft.

2. A woven tubing according to claim 1, wherein the monofilament has a flattening in the range of 1.2–5.0.

3. A woven tubing according to claim 1, wherein the cross-sectional shape of the monofilament is selected from the group consisting of elliptic, and flat shapes.

4. A woven tubing according to claim 1, wherein the monofilament has a size in the range of 30 to 80 dtex.

5. A woven tubing according to claim 1, wherein the weft comprises a multifilament having a single filament size in the range of 0.1–3.5 dtex and formed of 10–1000 single filaments.

6. A woven tubing according to claim 5, wherein the multifilament has a size in the range of 0.1 to 1.0 dtex.

7. A woven tubing according to claim 1, wherein the warp and weft are made of a polyester fiber, respectively.

8. A woven tubing according to claim 7, wherein the polyester fiber is at least one member selected from the group consisting of polyethylene terephthalate, polybutylene terephthalate, polyester-polyether block copolymers, and composite fibers thereof.

9. A woven tubing according to claim 1, wherein the tubing is a crimped tubing.

10. A woven tubing according to claim 1, wherein the tubing has a branched part.

11. A stent blood vascular prosthesis, comprising:

a woven tubing set forth in claim 1; and a stent to which the woven tubing is attached.

12. A woven tubing according to claim 2, wherein the monofilament has the flattening in the range of 1.5 to 3.0.

* * * * *

UNITED STATES PATENT AND TRADEMARK OFFICE
CERTIFICATE OF CORRECTION

PATENT NO. : 7,000,649 B2  
APPLICATION NO. : 10/390033  
DATED : February 21, 2006  
INVENTOR(S) : Yoshikazu Takahashi et al.

Page 1 of 1

It is certified that error appears in the above-identified patent and that said Letters Patent is hereby corrected as shown below:

Column 1, line 24, change "aorticaneurysm" to --aortic aneurysm--.

Column 12, claim 6, line 65, after "a" insert --single filament--.

Signed and Sealed this

Twenty-sixth Day of June, 2007

JON W. DUDAS  
*Director of the United States Patent and Trademark Office*